(12) United States Patent
Foster et al.

(10) Patent No.: US 9,194,786 B2
(45) Date of Patent: Nov. 24, 2015

(54) PARTICLE MANIPULATION SYSTEM WITH CYTOMETRIC CAPABILITY

(75) Inventors: John S. Foster, Santa Barbara, CA (US); Daryl W. Grummitt, Santa Barbara, CA (US)

(73) Assignee: Owl biomedical, Inc., Goleta, CA (US)

(*) Notice: Subject to any disclaimer, the term of this patent is extended or adjusted under 35 U.S.C. 154(b) by 668 days.

(21) Appl. No.: 13/507,830

(22) Filed: Aug. 1, 2012

(65) Prior Publication Data

US 2014/0034555 A1 Feb. 6, 2014

(51) Int. Cl.
*B01L 3/02* (2006.01)
*G01N 15/14* (2006.01)
*B01L 3/00* (2006.01)
*G01N 15/10* (2006.01)

(52) U.S. Cl.
CPC ...... *G01N 15/1484* (2013.01); *B01L 3/502761* (2013.01); *G01N 15/1459* (2013.01); *B01L 2200/0652* (2013.01); *B01L 2300/0816* (2013.01); *B01L 2300/0864* (2013.01); *B01L 2400/0454* (2013.01); *G01N 2015/1006* (2013.01); *G01N 2015/149* (2013.01)

(58) Field of Classification Search
CPC ........... G01N 15/1459; G01N 2015/1081
USPC ........................................................ 422/73
See application file for complete search history.

(56) References Cited

U.S. PATENT DOCUMENTS

| | | | |
|---|---|---|---|
| 6,838,056 B2 | 1/2005 | Foster | |
| 6,941,005 B2 | 9/2005 | Lary et al. | |
| 7,220,594 B2 | 5/2007 | Foster et al. | |
| 7,229,838 B2 | 6/2007 | Foster et al. | |
| 7,264,972 B2 | 9/2007 | Foster | |
| 7,745,221 B2 | 6/2010 | Butler et al. | |
| 2001/0055812 A1 | 12/2001 | Mian et al. | |
| 2004/0021073 A1* | 2/2004 | Barbic | B01F 13/0059 250/298 |
| 2005/0207940 A1* | 9/2005 | Butler et al. | 422/73 |
| 2007/0178529 A1 | 8/2007 | Breidford et al. | |
| 2008/0302732 A1* | 12/2008 | Soh | B01L 3/502761 210/695 |
| 2010/0225913 A1* | 9/2010 | Trainer | 356/338 |
| 2011/0189650 A1 | 8/2011 | Ayliffe et al. | |
| 2012/0122084 A1 | 5/2012 | Wagner et al. | |
| 2012/0190105 A1* | 7/2012 | Foster et al. | 435/288.7 |

FOREIGN PATENT DOCUMENTS

WO WO 2011/017681 2/2011

OTHER PUBLICATIONS

U.S. Appl. No. 13/374,899, filed Jan. 23, 2012, Foster, et al.
U.S. Appl. No. 13/374,898, filed Jan. 23, 2012, Foster, et al.

* cited by examiner

*Primary Examiner* — Jill Warden
*Assistant Examiner* — Brittany Fisher
(74) *Attorney, Agent, or Firm* — Jaquelin K. Spong (57) ABSTRACT

A MEMS-based particle manipulation system which uses a particle manipulation stage and a plurality of laser interrogation regions. The laser interrogation regions may be used to assess the effectiveness or accuracy of the particle manipulation stage. In one exemplary embodiment, the particle manipulation stage is a microfabricated, flap-type fluid valve, which sorts a target particle from non-target particles in a fluid stream. The laser interrogation stages are disposed in the microfabricated fluid channels at the input and output of the flap-type sorting valve. The laser interrogation regions may be used to assess the effectiveness or accuracy of the sorting, and to control or adjust sort parameters during the sorting process.

20 Claims, 12 Drawing Sheets

PARTICLE MANIPULATION SYSTEM WITH CYTOMETRIC CAPABILITY

CROSS REFERENCE TO RELATED APPLICATIONS

Not applicable.

STATEMENT REGARDING FEDERALLY SPONSORED RESEARCH

Not applicable.

STATEMENT REGARDING MICROFICHE APPENDIX

Not applicable.

BACKGROUND

This invention relates to a system and method for manipulating small particles in a microfabricated fluid channel.

Microelectromechanical systems (MEMS) are very small, often moveable structures made on a substrate using surface or bulk lithographic processing techniques, such as those used to manufacture semiconductor devices. MEMS devices may be moveable actuators, sensors, valves, pistons, or switches, for example, with characteristic dimensions of a few microns to hundreds of microns. A moveable MEMS switch, for example, may be used to connect one or more input terminals to one or more output terminals, all microfabricated on a substrate. The actuation means for the moveable switch may be thermal, piezoelectric, electrostatic, or magnetic, for example. MEMS devices may be fabricated on a semiconductor substrate which may manipulate particle passing by the MEMS device in a fluid stream.

For example, MEMS devices such as a movable valve, may be used as a sorting mechanism for sorting various particles from a fluid stream, such as cells from blood. The particles may be transported to the sorting device within the fluid stream enclosed in a microchannel, which flows under pressure. Upon reaching the MEMS sorting device, the sorting device directs the particles of interest such as a blood stem cell, to a separate receptacle, and directs the remainder of the fluid stream to a waste receptacle.

MEMS-based cell sorter systems may have substantial advantages over existing fluorescence-activated cell sorting systems (FACS) known as flow cytometers. Flow cytometers are generally large and expensive systems which sort cells based on a fluorescence signal from a tag affixed to the cell of interest. The cells are diluted and suspended in a sheath fluid, and then separated into individual droplets via rapid decompression through a nozzle. After ejection from a nozzle, the droplets are separated into different bins electrostatically, based on the fluorescence signal from the tag. Among the issues with these systems are cell damage or loss of functionality due to the decompression, difficult and costly sterilization procedures between sample, inability to sort sub-populations along different parameters, and substantial training necessary to own, operate and maintain these large, expensive pieces of equipment. For at least these reasons, use of flow cytometers has been restricted to large hospitals and laboratories and the technology has not been accessible to smaller entities.

A number of patents have been granted which are directed to such MEMS-based particle sorting devices. For example, U.S. Pat. No. 6,838,056 is directed to a MEMS-based cell sorting device, U.S. Pat. No. 7,264,972 b1 is directed to a micromechanical actuator for a MEMS-based cell sorting device. U.S. Pat. No. 7,220,594 is directed to optical structures fabricated with a MEMS cell sorting apparatus, and U.S. Pat. No. 7,229,838 is directed to an actuation mechanism for operating a MEMS-based particle sorting system. Additionally, U.S. patent application Ser. No. 13/374,899 and Ser. No. 13/374,898 provide further details of other MEMS designs. Each of these patents and patent application publications is hereby incorporated by reference, and each is assigned to Innovative Micro Technology and Owl biomedical, the assignee of the present invention.

SUMMARY

One feature of the MEMS-based particle sorting system is that the fluid may be confined to small, microfabricated channels formed in a semiconductor substrate throughout the sorting process. The MEMS device may be a valve which separates a target particle from other components of a sample stream. The MEMS device may redirect the particle flow from one channel into another channel, when a signal indicates that a target particle is present. This signal may be a photon from a fluorescent tag which is affixed to the target particle and excited by laser illumination in an interrogation region upstream of the MEMS device. Thus, the MEMS device may be a particle or cell sorter operating on a fluid sample.

More generally however, particles in the fluid stream may be manipulated rather than sorted, by some manipulation including heating, tagging, charging, altering or destroying a target particle flowing in a fluid stream. In this scenario, the target particle may be distinguished from the non-target particle by a fluorescence activated detection, such as that used in the above-described FACS flow cytometers. The identified cells may then be manipulated by the particle manipulation stage. This manipulation may be accomplished by a microfabricated device manufactured on a substrate which heats, tags, charges, alters or destroys the target particles. The fabrication substrate may also include microfabricated channels leading to and from the particle manipulation stage.

A system and method are described which makes use of this architecture which is particular to the particle manipulation systems such as those disclosed in the aforementioned patents. These techniques may form a particle manipulation system with cytometric capability, as described below. A microfabricated device may be used to manipulate the particles in the fluid stream enclosed in the microfabricated channel. In this system and method, a plurality of interrogation regions exist within the microfluidic pathways, with one laser interrogation region upstream of the MEMS device, and at least one additional laser interrogation region downstream of the MEMS device. The additional laser interrogation regions may be used to confirm the performance of the microfabricated manipulation device.

Accordingly, the particle manipulation system with cytometric capability may include laser light directed into a first laser interrogation region in first portion of a microchannel formed in a substrate, at least one particle manipulation stage formed in the substrate, and laser light directed into at least one additional laser interrogation region formed in a second portion of a microchannel formed in the substrate, wherein the first portion of the microchannel is disposed upstream of the particle manipulation stage, and the second portion of the microchannel is disposed downstream of the particle manipulation stage, and the particle manipulation stage comprises a movable structure microfabricated on the substrate which includes the microfluidic channels.

In one embodiment, the MEMS device is a flap-type cell sorter, which sorts a target cell (cancer cell, sperm cell, stem cell for example) from the other components of a fluid stream. The MEMS sorter may be a flap or diverter which is pulled down into the channel to redirect the flow in response to the detection of a target particle in the channel. This flap directs the flow into a sort channel rather than the waste channel.

In one embodiment, the additional interrogation region may be disposed in the sort channel, where the target particles are directed by the MEMS sorter. By counting the proportion of target particles to non-target particles, the effectiveness of the sorter can be ascertained, and properties or parameters can be adjusted as the sorting process is underway.

These and other features and advantages are described in, or are apparent from, the following detailed description.

BRIEF DESCRIPTION OF THE DRAWINGS

Various exemplary details are described with reference to the following figures, wherein.

DETAILED DESCRIPTION

The system described herein is a particle sorting system which may make use of microchannel architecture of a particle manipulation system, such as those disclosed in the aforementioned patents. More generally, the systems and methods describe a particle manipulation system with multiple laser interrogation regions, which form a particle manipulation system with cytometric capability. The multiple laser interrogation regions may provide information as to the effectiveness or accuracy of the particle manipulations, allowing the manipulations to be adjusted or controlled during the process.

In the figures discussed below, similar reference numbers are intended to refer to similar structures, and the structures are illustrated at various levels of detail to give a clear view of the important features of this novel device.

Figure 1A:
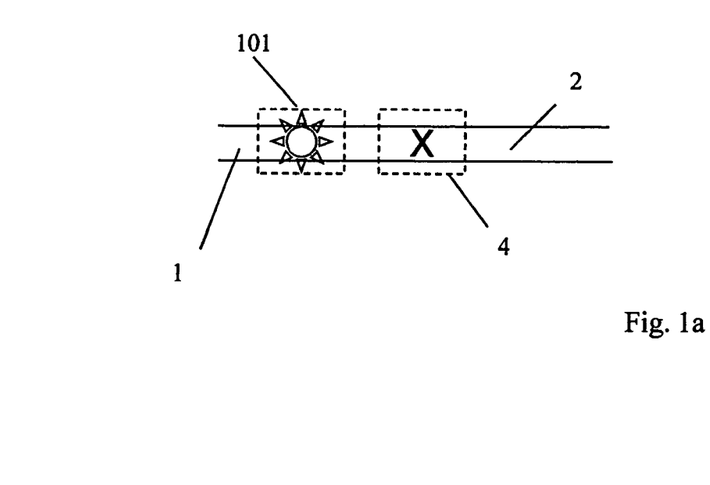
FIG. 1a is a simplified illustration of a microfabricated particle manipulation system.

FIG. 1a is a schematic illustration of a MEMS-based particle manipulation system using lithographically formed microfluidic channels. One microfluidic channel 1 may be an input channel which directs a fluid flow. The fluid stream in microfluidic channel 1 flows through a first laser interrogation region 101. In this region, light from one or more lasers is directed. The light may be focused to a spot and onto the particles flowing in the stream, wherein the laser interrogation region 101 is disposed upstream of a microfabricated manipulation stage 4. If the particles have the appropriate fluorescent tag affixed thereto, the tag may be excited and emit a characteristic fluorescent photon. This photon may be detected by optical detectors and evaluated by appropriate logic circuits. The logic circuits may control the manipulation stage 4, which may manipulate the tagged particles under the control of the logic circuits.

In one exemplary embodiment, the MEMS device may apply a charge to the target particle. In another exemplary embodiment discussed further below, the manipulation stage 4 may be an actuator, which diverts the target particle into a different flow path as the non-target particles.

Figure 1B:
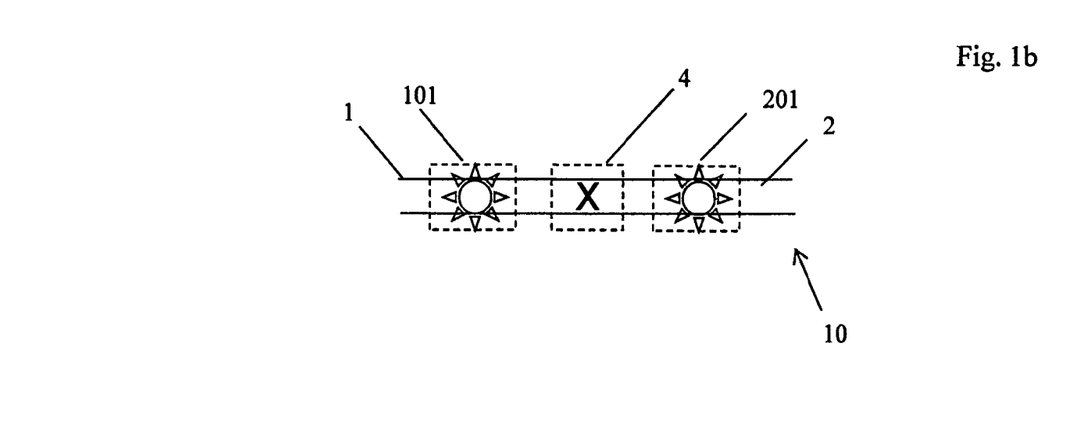
FIG. 1b is a simplified illustration of a microfabricated particle manipulation system according to the present invention.

FIG. 1b is a schematic illustration of a particle manipulation system with cytometric capability 10, which uses lithographically formed microfluidic channels, according to the present invention. One microfluidic channel 1 may be an input channel which directs a fluid flow into a manipulation stage 4. Microfabricated device 4 may alter the trajectory, morphology, shape, charge or other characteristic of the particle. Another microfluidic channel 2 directs the fluid flow away from the manipulation stage 4 and into an output channel. A second laser interrogation region 201 may be positioned in microfluidic channel 2. Using laser interrogation region 201 to interrogate the passing particles, the effectiveness, accuracy and/or efficiency of MEMS manipulation stage 4 can be assessed. The simultaneous detection of fluorescence and the manipulated characteristic indicates accurate performance of the manipulation stage.

For example, manipulation stage 4 may apply a charge to a passing particle. Laser interrogation stage 2 may confirm the presence of both the charge and the fluorescent tag by measuring the voltage on a parallel plate capacitor (not shown) installed in the channel 2. By so doing, the coincidence of both the fluorescence and the voltage signal is evidence that the charge is correctly place on tagged particles. In the case of a particle or cell sorter, the presence of the target sorted particle in the sort passage where the additional laser interrogation stage 201 is placed, may indicate correct and effective sorting.

Figure 2A:
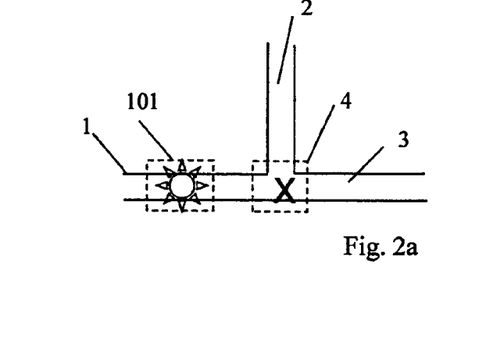
FIG. 2a is a simplified illustration of a microfabricated particle manipulation system having an intersection.
Figure 2B:
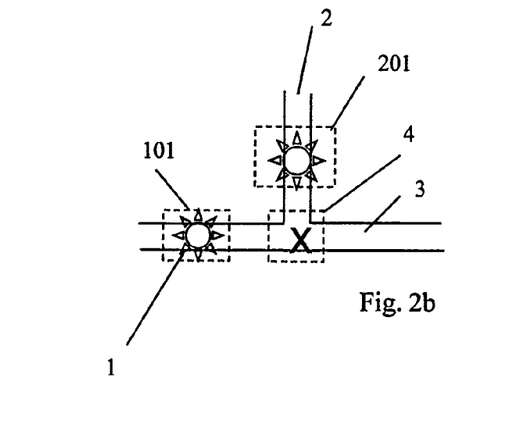
FIG. 2b is a simplified illustration of a microfabricated particle manipulation system having an intersection according to one embodiment of the present invention.

FIG. 2a is a schematic illustration of another particle manipulation system with cytometric capability, using lithographically formed microfluidic channels. In FIG. 2a, two or more channels are formed at the output of the manipulation stage 4, forming an intersection point. One channel 2 may move in one path away from the manipulation stage 4, whereas another channel 3 may move in another path away from manipulation stage 4. FIG. 2b depicts a particle manipulation system with cytometric capability. As shown in FIG. 2b, channel 2 may be equipped with an additional laser interrogation stage 201, which may identify the various particles according to their response to irradiation with laser light. If a particle emits a photon in response to irradiation, that is an indication that it is a tagged, target particle. If it does not, it is likely an untagged, non-target particle.

Figure 2C:
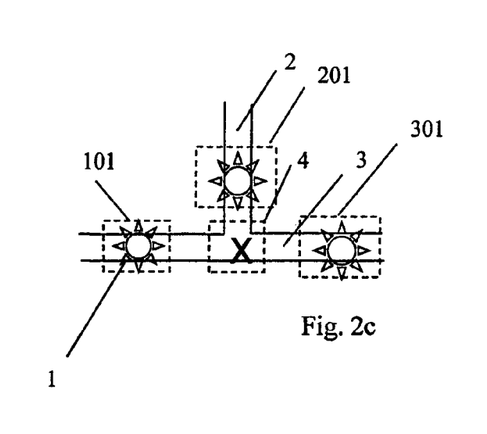
FIG. 2c is a simplified illustration of a microfabricated particle manipulation system having an intersection according to another embodiment of the present invention.

As shown in FIG. 2c, both channels 2 and 3 may be equipped with an additional laser interrogation stage 201 and laser interrogation stage 301, which may identify the various particles according to their response to irradiation with laser light. Indeed, any number of additional laser interrogation regions may be placed in any number of microfluidic channels, although large numbers of such regions may become difficult to separate, as described more fully below. As before, if a particle emits a photon in response to irradiation, that is an indication that it is a tagged, target particle. If it does not, it is likely an untagged, non-target particle. These two laser interrogation stages may measure the difference in density of target particles in one channel 2 relative to the other channel 3 or input channel 1.

Figure 3A:
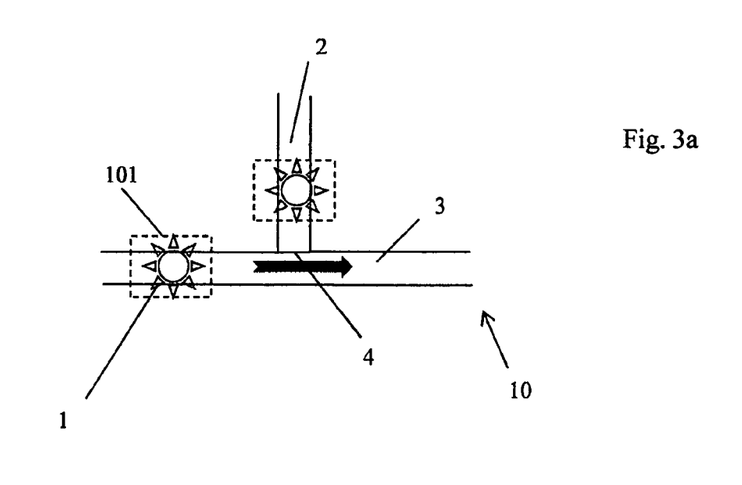
FIG. 3a is a simplified illustration of a microfabricated particle sorting system according to one embodiment of the present invention, with the sort valve in the closed position.

FIG. 3a is a schematic illustration of a particle manipulation system with cytometric capability 10 using multiple laser interrogation regions disposed in lithographically formed microfluidic channels. The manipulation stage 4 may be a MEMS flap-type actuator or sorter. The MEMS flap-type actuator is shown only schematically in FIG. 5, and may be a flap-type fluidic valve which separates a target particle from a remainder of the sample stream, based on a signal from the first laser interrogation region. The MEMS flap-like actuator may be a simple, hinge mounted movable member that may be drawn downward in response to a force acting on the movable member. The force may be, for example, electrostatic, magnetostatic or electromagnetic. The movable member may be formed lithographically on a silicon substrate, and methods for manufacturing such a device may be found in the above-incorporated patents and patent applications.

The MEMS actuator may divert the incoming fluid stream into one of the plurality of exit channels, for example into either channel 2 or channel 3. For example, if a signal from laser interrogation region 101 indicates that a target particle is present, the logic circuit coupled to laser interrogation region 101 may send a signal to the MEMS actuator 4 to activate the flap. Drawing down the flap will divert the detected target particle into the sort channel 2 rather than allowing it to flow past into waste channel 3.

Figure 3B:
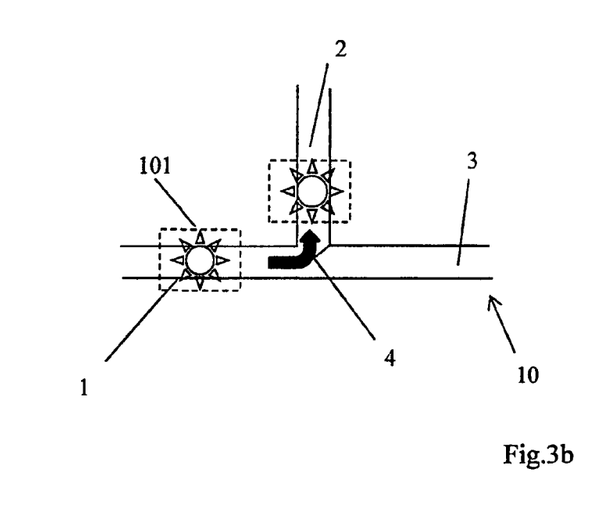
FIG. 3b is a simplified illustration of a microfabricated particle sorting system according to one embodiment of the present invention, with the sort valve in the open position.
Figure 4A:
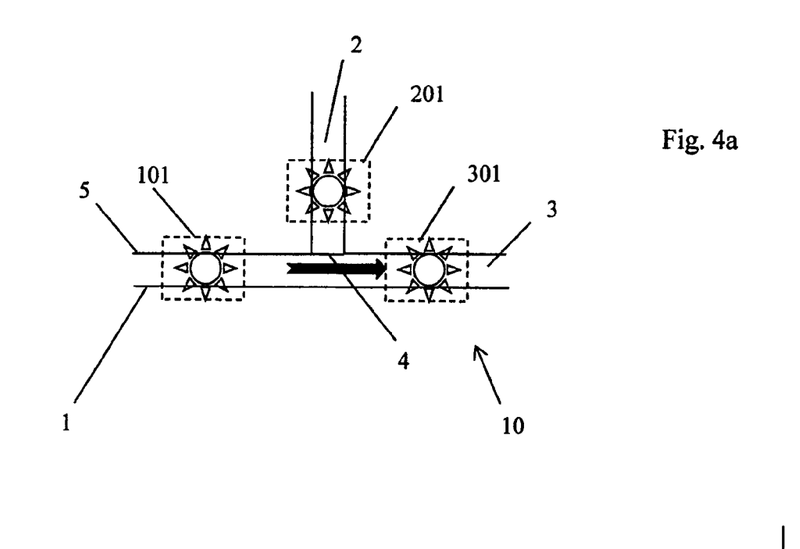
FIG. 4a is a simplified illustration of a microfabricated particle sorting system according to another embodiment of the present invention, with the sort valve in the closed position.
Figure 4B:
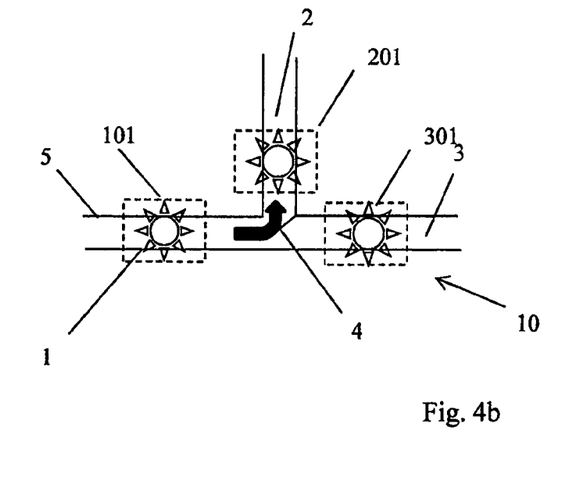
FIG. 4b is a simplified illustration of a microfabricated particle sorting system according to another embodiment of the present invention, with the sort valve in the open position.

As mentioned previously, waste channel 3 may also be equipped with an additional laser interrogation region 301. This arrangement is shown in FIGS. 4a and 4b, which are similar to FIGS. 3a and 3b, except that two laser interrogation regions 201 and 301 are disposed in sort channel 2 and waste channel 3, respectively. The two additional interrogation regions 201 and 301 may measure the increased density of target cells in sort channel 2 compared to waste channel 3, and thus may provide evidence of the effectiveness and accuracy of the MEMS sorter 4 and laser interrogation region 101.

Thus, as can be seen from the figures above, the additional laser interrogation regions 201 and 301 (or more) may act as a cytometer or as a quality control measure. The system 10 may give feedback as to the correct setting of any adjustable parameters in the sorting algorithm. Such parameters may include, for example, fluorescent pulse shape, width, magnitude or duration, laser intensity, optical alignment or focusing. These parameters may then be adjusted during the sort, rather than waiting for the entire sample to be processed before finding a problem in the sorting. The presence of additional laser interrogation regions 201 and/or 301 may provide cytometer capability to the sorter, in that it is able to count, enumerate, or quantify the density or purity of the sorted sample, while the sorting process is underway. This capability may allow the sort process to be adjusted in real time, that is, while it is underway. This may allow an optimization of sort parameters without performing multiple sorting operations on a sample, thus saving time and sample volume.

Figure 5:
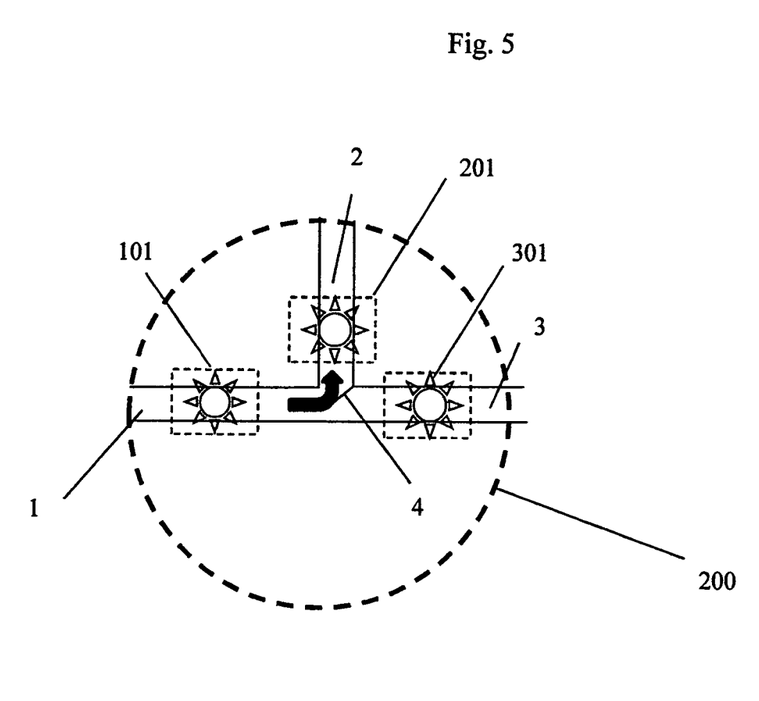
FIG. 5 is a simplified illustration of a microfabricated particle sorting system according to an embodiment of the present invention, showing the field of view of the detector compared to the interrogation regions.

Also shown in FIG. 5 is the field of view 200 of the detector monitoring laser interrogation region 101 as well as additional laser interrogation regions 201 and 301. As indicated in FIG. 5, all laser interrogation regions may fall within the detector field of view, and thus may share at least a portion of the optical and electronic data detection channel. Accordingly, light collected from the at least one additional laser interrogation region is collected by an optical system which also collects light from the first laser interrogation region. Details as to how to exploit or implement this feature are set forth below with respect to the remaining figures.

Figure 6:
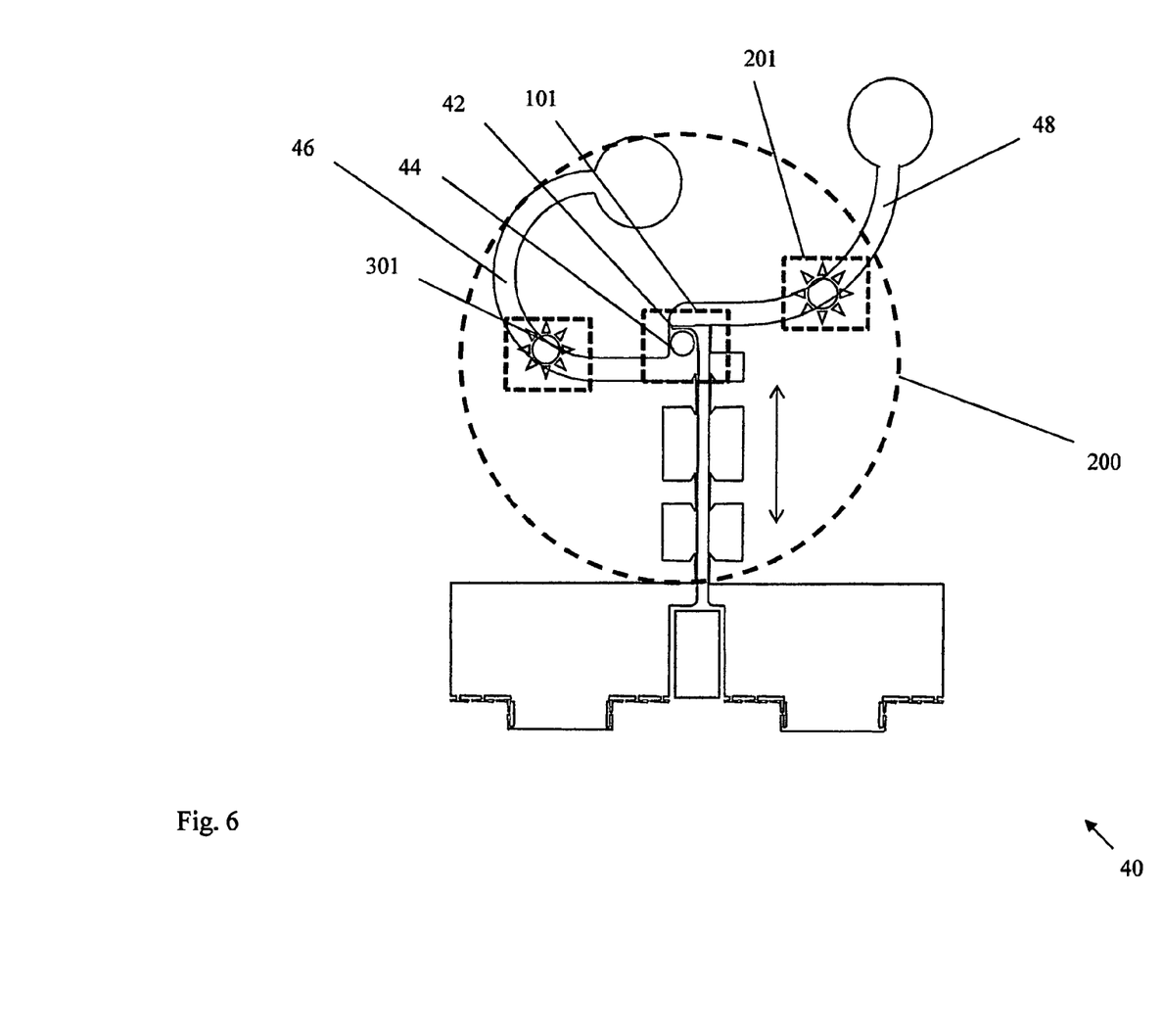
FIG. 6 is a simplified illustration showing further detail of one embodiment of a microfabricated particle sorting system according to the present invention.

FIG. 6 shows another exemplary embodiment of a particle manipulation system with cytometric capability 40. FIG. 6 shows details of an actual implementation of the plurality of laser interrogation regions on a MEMS actuator in a particle manipulation system 40. In this diagram, a sort channel 48 flows upward from the diverter and the waste channel 46 flows downward, and the diverter is positioned at the bottom of a vertical channel 44 (perpendicular to the paper). This actuator may use a magnetically actuated diverter 42, to shift the fluid flow exiting a vertical channel 44 from the lower, waste channel 46 to the upper, sort channel 48. The diverter may be actuated in response to a fluorescent signal emanating from a target cell which has been tagged with a fluorescent marker. This "fluorescence activated cell sorting" (FACS) technique is similar to the detection methodologies used in flow cytometers. The detection occurs in the first laser interrogation region 101 disposed in the vertical channel 44 as shown in FIG. 6. The success or failure of the sorting can be confirmed by disposing an additional laser interrogation region 201 and/or 301 in either or both of the sort channel 48 and waste channel 46, respectively. Additional details relating to the design and manufacture of the microfabricated electromagnetic diverter may be found in the incorporated patents.

As shown in FIGS. 5 and 6, the approximate field of view of the detection optics may cover all laser interrogation regions 101, 201 and 301, as described in greater detail below. Of note in FIGS. 5 and 6, since the field of view of the detection optics is sufficiently large to include laser interrogation region 101, as well as laser interrogation region 201, and even laser interrogation region 301, or more, the multiple laser interrogation regions may share at least a portion of an optical detection path. This is a result of the small scale of the microfabricated cell sorter and associated microfluidic channels. Each of the channels 1, 2 and 3 is on the order of 20 microns in width. The distance between laser interrogation region 1 and MEMS cell sorter 4 may be kept below 500 microns or so, in order to reduce the timing uncertainty between the passage of the target particle and the opening of the MEMS cell sorting valve 4. As this distance gets longer, the additional uncertainty may mean that a non-target particle is allowed into the sort channel 2, or a target particle is allowed to pass into waste channel 3. Either of these events reduces the purity or the yield of the sorted sample. Accordingly, to optimize the sort performance, the distance between the detection region and the sorter may be kept as short as practical.

While the particle manipulation in this embodiment is a cell sorter, it should be understood that any number of particle manipulations may be performed, such as tagging, charging, heating, altering and destroying rather than sorting.

In general, the valves, actuators or manipulators 4 used herein may be formed on a semiconductor substrate using lithographic techniques well known in MEMS fabrication. Details of their fabrication techniques may be found in the aforementioned patents. Thus, a characteristic dimension, for example its total width or length of the structure may be about 500 microns or less, and the fluidic channels may be formed in the same substrate with characteristic dimensions of about 10-20 microns.

For the same reason, the laser interrogation regions 2 and 3 should also be located ideally near the manipulation stage 4 as well. These considerations lead to the small dimensions of the structure, and these dimensions are also well suited to lithographic processing methodologies as described in the incorporated patents and patent applications.

However, the result of these dimensions is that the additional laser spots fall into the same field of view, and therefore may be processed by the same optical channel. Accordingly, measures may be taken to separate the data falling in the same optical channel but emanating from different laser interrogation regions. These measures may include altering the trajectory, spectral content, timing and/or duration of the laser energy directed into these additional laser interrogation regions. Alternatively, separate laser sources and detection optics may be provided. Various embodiments of achieving this separation are described more fully below.

Figure 7:
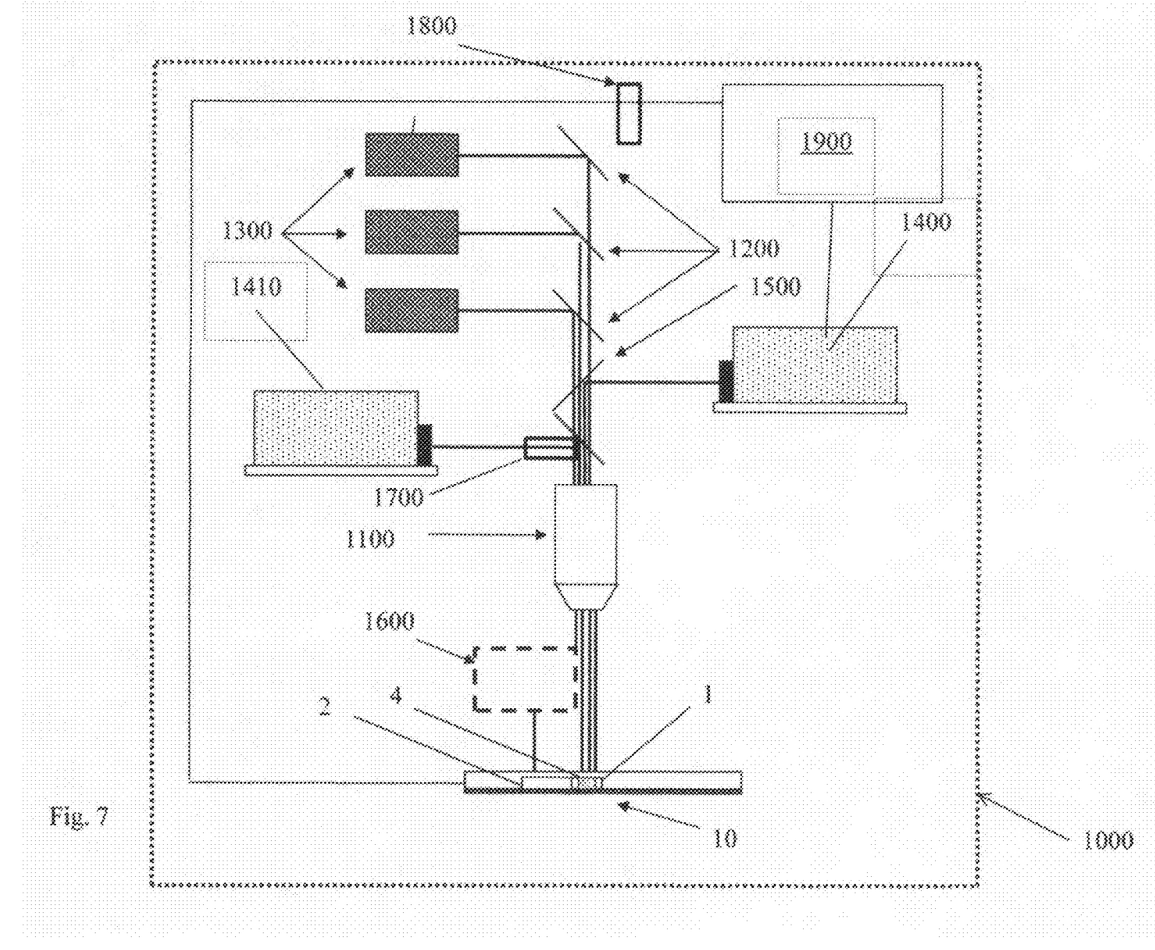
FIG. 7 is a simplified system-level illustration of a microfabricated particle sorting system according to the present invention, showing the placement of the various optical components.

FIG. 7 is a schematic illustration of the particle manipulation system 1000 using multiple laser interrogation regions as described above. In particular, FIG. 7 lays out the optical path of the interrogating laser and detection optics.

In one embodiment of system 1000, the target particle may be a particular cell, such as a stem cell, or a cancer cell, which has been tagged with a fluorescent marker. This marker emits photons having a particular energy when irradiated with a laser 1400 operating at a predefined wavelength. Accordingly, in this cell sorting system, a laser source 1400 may be directed by a turning mirror 1500 through the detection optics 1100 onto the MEMS chip 100 in the detection region 160 shown in FIG. 1. The optical axis of the detection optics 1100 and the laser source 1400 may be collinear, at least over a portion of the optical path. Thus, the orientation of the laser application and optical detection along this optical axis may be perpendicular or orthogonal to the substrate fabrication plane, orthogonal to the plane of motion of the sorter flap movable structure 4 and orthogonal to the flow of the sample fluid through the detection region. This may have important consequences as the light traverses the surfaces with an orthogonal angle of incidence, which may reduce specular reflection and thus reduce or eliminate a noise source in the detection scheme.

The fluorescence emitted from the irradiated particles may be shaped by detection optics 1100 and separated by dichroic mirrors 1200 and directed into a bank of photodetectors 1300. A plurality of photodetectors may accommodate multiple wavelengths of emitted light, for multiparametric detection. The signal output by the photodetectors 1300 indicates the presence or absence of the target particle in the detection region 101. The signal may be delivered to a controller 1900, which manages the relative timing of the components in the particle sorting system 1, and collects the data. The controller 1900 may be a general purpose computer or a specialized circuit or ASIC. Upon detection of the target particle, a signal is generated by the controller 1900 which energizes the force-generating or flux-generating apparatus. The force generating apparatus is a device which causes a force to arise in the movable structure 4 itself, causing the motion of the movable structure. This force-generating apparatus may not directly mechanically coupled to the movable structure 4. For example, the force-generating apparatus may be a source of magnetic flux which causes a magnetostatic force to arise in an inlaid permeable material in the movable structure 4. This force may pull the flap or movable structure toward the force-generating apparatus, opening the sort channel 2 and closing the waste channel 3. Importantly, the force-generating apparatus may reside in the particle sorting system 1000, rather than in the actuator structure 4. As mentioned previously, this may reduce the cost and complexity of the actuator structure 4. Another optional laser 1410 may also be included to provide a second optical channel.

In the detection region 101, the target particle may be distinguished from the other constituents of the fluid sample. The detection means may be, but is not necessarily, a laser 1400 and associated optics, which directs the laser to a spot upstream of the movable diverter 42, and generally in detection region 101. The detection means may be based on any number of characteristics or attributes that distinguish the target particle from the others in the fluid stream. For example, the particles may be distinguished by, for example, differences in an electrical attribute, a hydrodynamic attribute, a magnetic attribute, an optical attribute, a thermal attribute, mass, and a mechanical attribute of the particle, to name just a few. This list is not meant to be exhaustive, but instead to provide examples of detection systems which may be used with the actuator described herein.

In one embodiment, the target particle may be a particular cell which may be tagged with a fluorescent tag, which emits light of a particular color when irradiated by a laser at a particular wavelength. Such tags are well known in the field and include for example fluorescein, Texas Red, phycobiliproteins, cyanine derivatives and rhodamine. While much of this disclosure is directed to this application, it should be understood that the systems and methods described herein are also applicable to other detection mechanisms used to distinguish particles one from another. These mechanisms may be well known, or may yet be invented.

Upon passing through the detection region 101, a signal is generated by the detector (not shown) indicating that a target particle is present in the first interrogation region 101. After a known delay, a signal is generated by a controller which indicates that the sorting gate, i.e. the movable diverter 42, or flap-like actuator 10, is to be opened, in order to separate the target particle which was detected, from the other components in the fluid stream. The movable diverter 42 or flap-like actuator 10 may comprise permeable magnetic materials, so that a magnetic force may arise between them when a magnetic field is present. When the signal is generated by the controller, a force is generated between the embedded magnetically permeable material in the diverter 42 or flap-like actuator 10, which draws the diverter 42 or actuator 10 downward. This motion closes off waste channel 3 or 48 and redirects the target particle into a sort channel 2 or 46. The sorted sample is subsequently collected from a sort reservoir at the end of the sort channel 2 or 46, which holds the sorted sample.

The microfabricated particle manipulation device 10 or 40 may be inserted into a housing containing the components shown in FIG. 5. The insertion area may be a movable stage with mechanisms available for fine positioning of the particle manipulation device 10 or 40 and associated microfluidic channels against one or more data, which orient and position the detection region and particle manipulation device 10 or 40 with respect to the collection optics 1100. If finer positioning is required, the input stage may also be a translation stage, which adjusts the positioning based on observation of the location of the movable diverter 42 or flap-like actuator 4 relative to the datum.

The MEMS particle sorting system 1000 shown in FIG. 7 may include a number of elements that may be helpful in implementing the additional interrogation regions 201 and 301, or more. First, an optical manipulating means 1600 may alter the trajectory, spectral content, timing or duration of the laser radiation from laser 1400 to the second or third interrogation spots. Examples of items that may be included in optical manipulating means 1600 are a birefringent crystal, spinning prism, mirror, saturable absorber, acousto-optic modulator, harmonic crystal, Q-switch, for example. More generally, optical manipulating means 1600 may include one or more items that alter laser frequency, amplitude, timing or trajectory along one branch of the optical path to an additional interrogation region.

For example, optical manipulating means 1600 may include a beamsplitter 1620 and photoacoustic modulator 1640. The beam splitter 1620 may separate a portion of the incoming laser beam into a secondary branch or arm, where this secondary branch or arm passes through the modulator which modulates the amplitude of the secondary beam at a high frequency. The modulation frequency may be, for example, about 2 MHz or higher. The light impinging on the first laser interrogation region 101 may, in contrast, be continuous wave (unmodulated). The secondary branch or arm is then directed to the additional laser interrogation region 201 or 301. This excitation will then produce a corresponding fluorescent pattern from an appropriately tagged cell.

This modulated fluorescent pattern may then be picked up by the detection optics 1600, which may recombine the detected fluorescence from interrogation region 201 and/or 301 with fluorescence from laser interrogation region 101. The combined radiation may then impinge on the one or more detectors 1300.

An additional optical component 1700 may also alter the frequency, amplitude, timing or trajectory of the second beam path, however, it may perform this operation upstream (on the detector side) of the objective lens 1100 rather than downstream (on the sample side) of it, as does optical component 1600.

Figure 9:
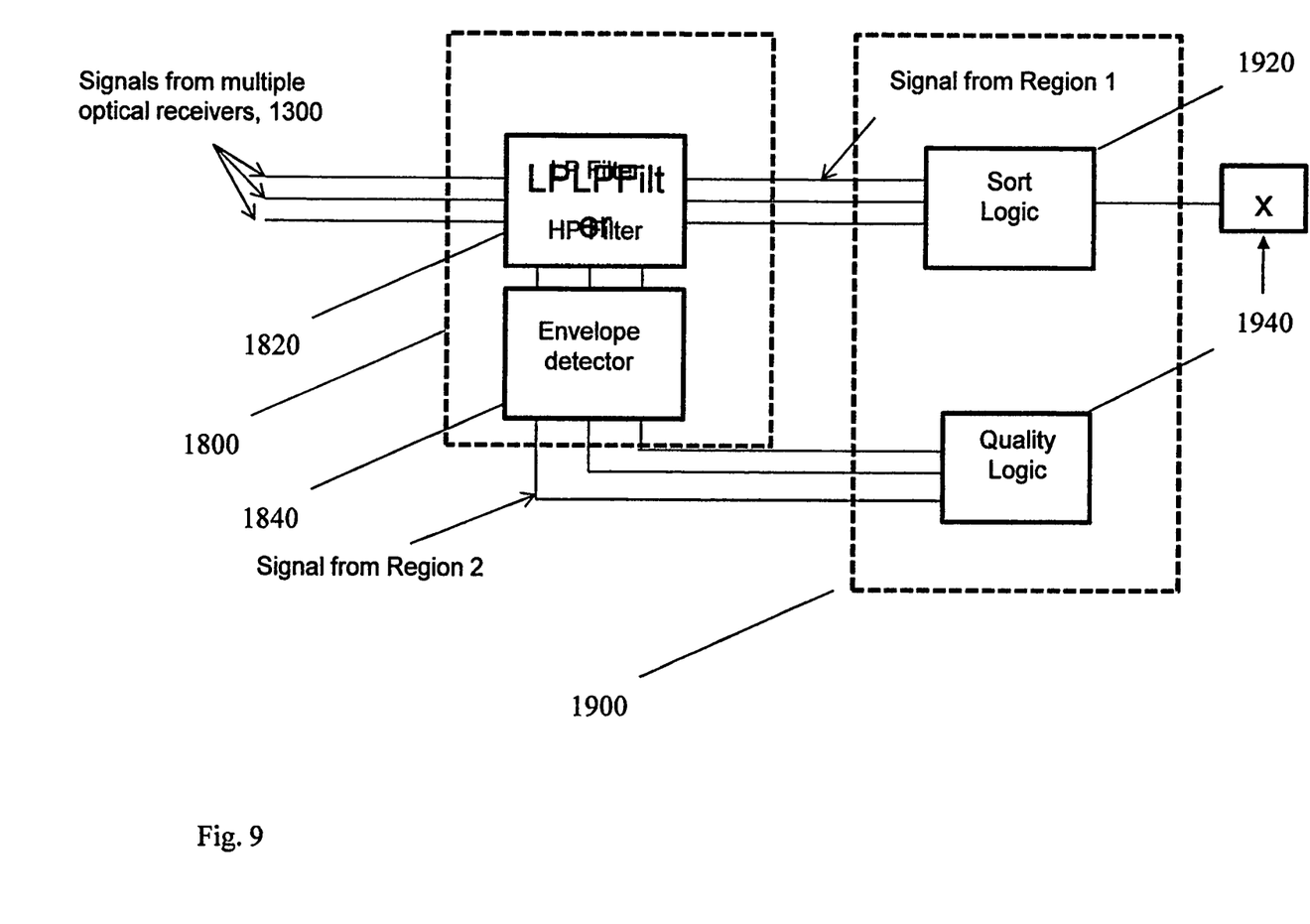
FIG. 9 shows further detail of another of the components of the optical detection system of the microfabricated particle sorting system.

The output of detectors 1300 may be analyzed to separate the content corresponding to region 201 and/or region 301 from the content corresponding to laser interrogation region 101. This may be accomplished by applying some electronic distinguishing means to the signals from detectors 1300. As shown in FIG. 9, the electronic distinguishing means 1800 may include electronic circuitry that distinguishes the signals coming from laser interrogation region 101 from those of laser interrogation regions 201 and/or 301. The details of electronic distinguishing means 1800 may depend on the choice for optical manipulation means 1600. For example, filter 1820 may include a high pass stage and a low pass stage that is consistent with the photoacoustic modulator 1640.

Figure 8:
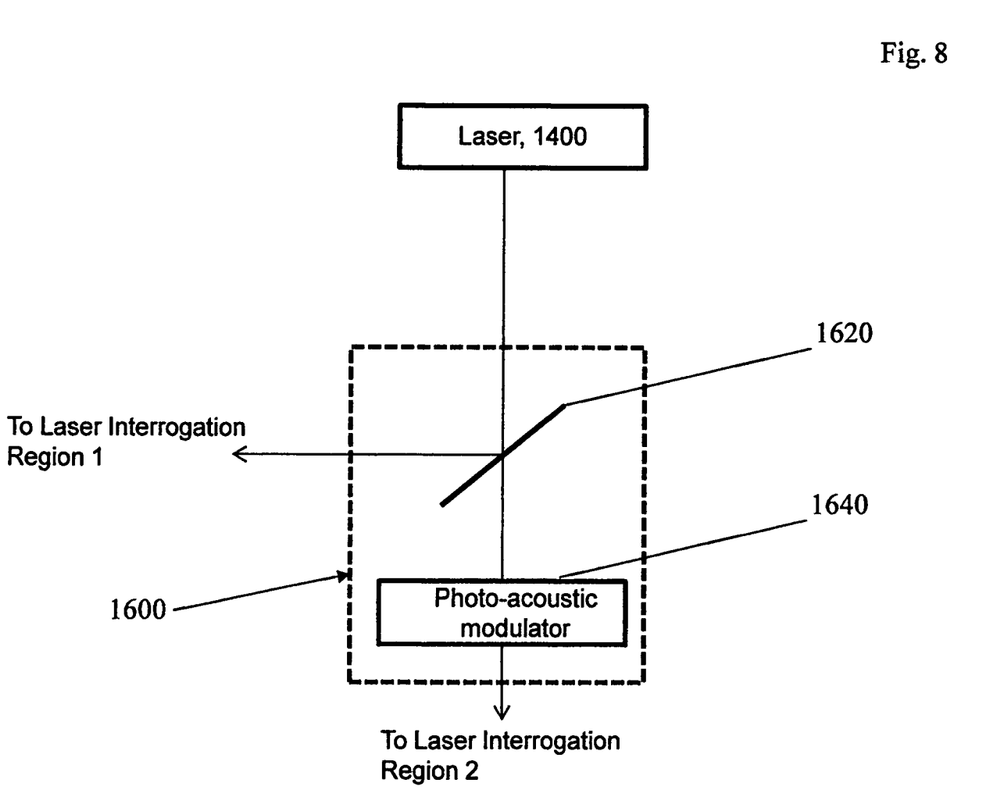
FIG. 8 shows further detail of one of the components of the optical detection system of the microfabricated particle sorting system.
Figure 10A:
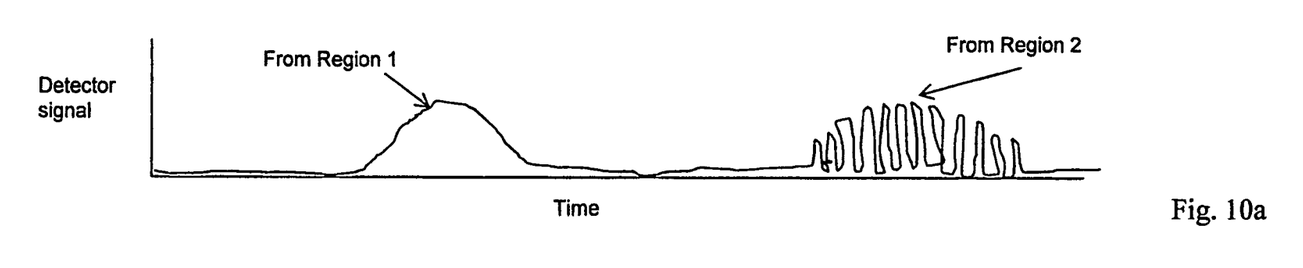
FIG. 10a is a representation of a signal waveform from the optical detector, showing the difference in pulse shape from region 1 relative to region 2.

FIGS. 8, 9 and 10 describe in further detail one exemplary embodiment of the particle manipulation system with multiple laser interrogation regions 1000. In FIG. 8, a particular selection for the optical manipulator means 1600 is illustrated. Optical manipulating means 1600 may include the beamsplitter 1620 and photoacoustic modulator described previously. In this embodiment, the electronic distinguishing means may have the architecture shown in FIG. 9, and consistent with this choice of optical manipulating means 1600. FIG. 10 shows the signal from the multiple optical detectors 1300 being analyzed by electronic distinguishing means 1800. Electronic distinguishing means 1800 includes a filter 1820 (high pass and/or low pass) and an envelope detector 1840.

Figure 10B:
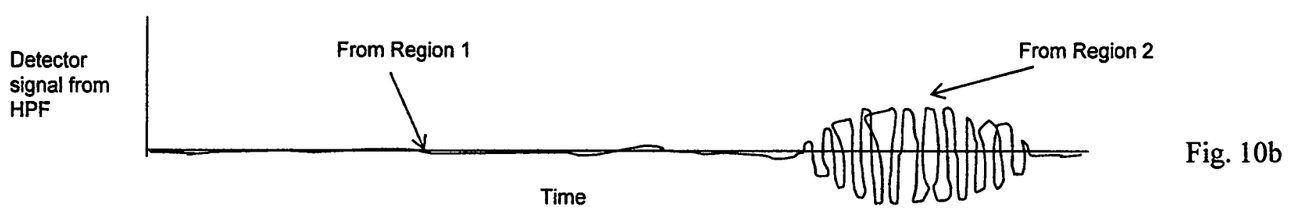
FIG. 10b is a representation of a signal waveform from the optical detector, showing the difference in pulse shape from region 1 relative to region 2, after high pass filtering.
Figure 10C:
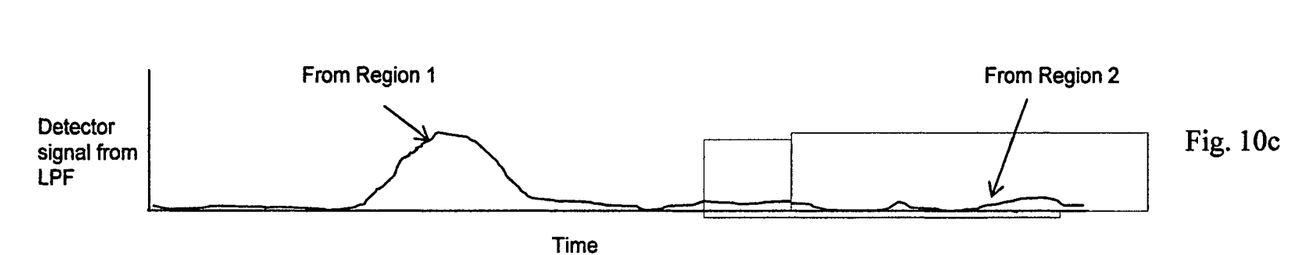
FIG. 10c is a representation of a signal waveform from the optical detector, showing the difference in pulse shape from region 1 relative to region 2, after low pass filtering.

The unfiltered signal output from detectors 1300 may appear as shown schematically in FIG. 10*a*. The data shown in FIGS. 10*a*-10*c* are illustrative of data that may be generated by the system 1000, and show the detector output signal amplitude as a function of time. The signal may include a continuous wave portion and a modulated portion. After filtering through the high pass filter stage, the signal may appear as shown in FIG. 10*b*, and after the low pass stage as shown in FIG. 10*c*. These signals may then be easily separated in the logic circuits of computer 1900. Alternatively, the high pass filter may be an envelope detector 1840, which puts out a signal corresponding to the envelop of the amplitudes of the high frequency pulses.

Other sorts of components may be included in electronic distinguishing means 1800 to separate the signals. These components may include, for example, a signal filter, mixer, phase locked loop, multiplexer, trigger, or any other similar device that can separate or distinguish the signals. Component 1800 may also include the high pass and/or low pass electronic filter or the envelope detector described previously. The two sets of signals from the electronic distinguishing means 1800 will be handled differently by the logic circuits as will be described next.

The output of the low pass filter may pass the low frequency components which are associated with laser interrogation region 101 and the high pass filter may pass the higher frequency, amplitude modulated components corresponding to laser interrogation region 201 and/or 301. The low pass component may pass to the sort logic circuits 1920 of computer or ASIC 1900, and the high frequency components may pass to the quality assessment circuits 1940 of computer or ASIC 1900. The computer or ASIC 1900 may then control the opening or closing of the flap-like movable structure 10 or diverter 42 with the sort logic circuits 1920, and the quality assessment circuits 1940 may generate an output indicative of the quality, effectiveness or accuracy of the sorting process. Based on the indications from quality assessment circuits 1940, parameters of the sorting can be adjusted to obtain a particular result in the quality assessment circuits 1940. Accordingly, in particle manipulation system 1000, the signals from the at least one additional laser interrogation region are coupled to logic circuits, and the logic circuits are coupled to the particle manipulation stage to control, monitor or adjust a cell sorting process.

Figure 11:
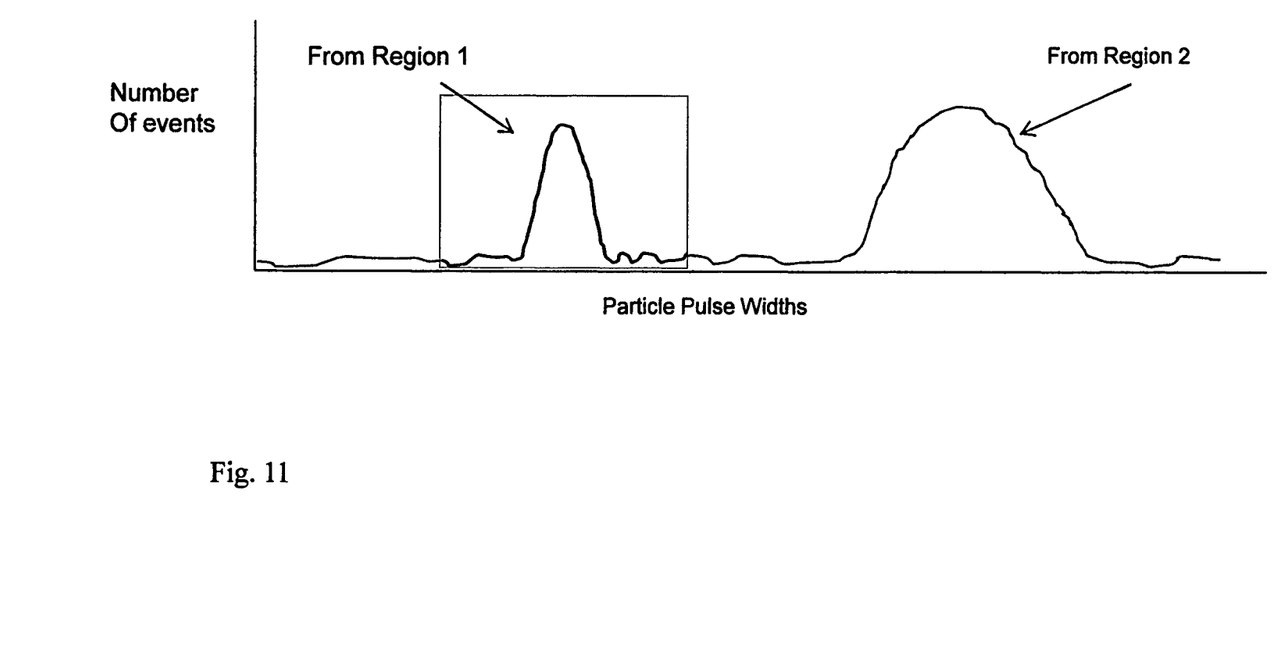
FIG. 11 is a representation of a signal waveform from the optical detector, showing the difference in pulse width from region 1 relative to region 2.

In another exemplary embodiment, the signals from region 201 and/or 301 may be separated according to pulse width. It is known that the pulse width from downstream particles may be wider than the pulse widths from upstream particles, even if the interrogation laser spot is equivalent. This is a result of the slower flow in downstream channel due to the bifurcation of fluid at the sorting point. One can use geometry (e.g. channel width) to control the velocity (and therefore pulse width) as well. An illustrative signal is shown in FIG. 11, which is an illustrative histogram of the number of signal events having a given pulse width. The two populations of different pulse widths are shown in FIG. 11. Accordingly, a detector may be used which distinguishes the signals based on these pulse widths, with the wider pulse widths corresponding to further downstream portions of the fluid flow, and thus to interrogation regions 201 and/or 301 rather than first interrogation region 101.

Figure 12:
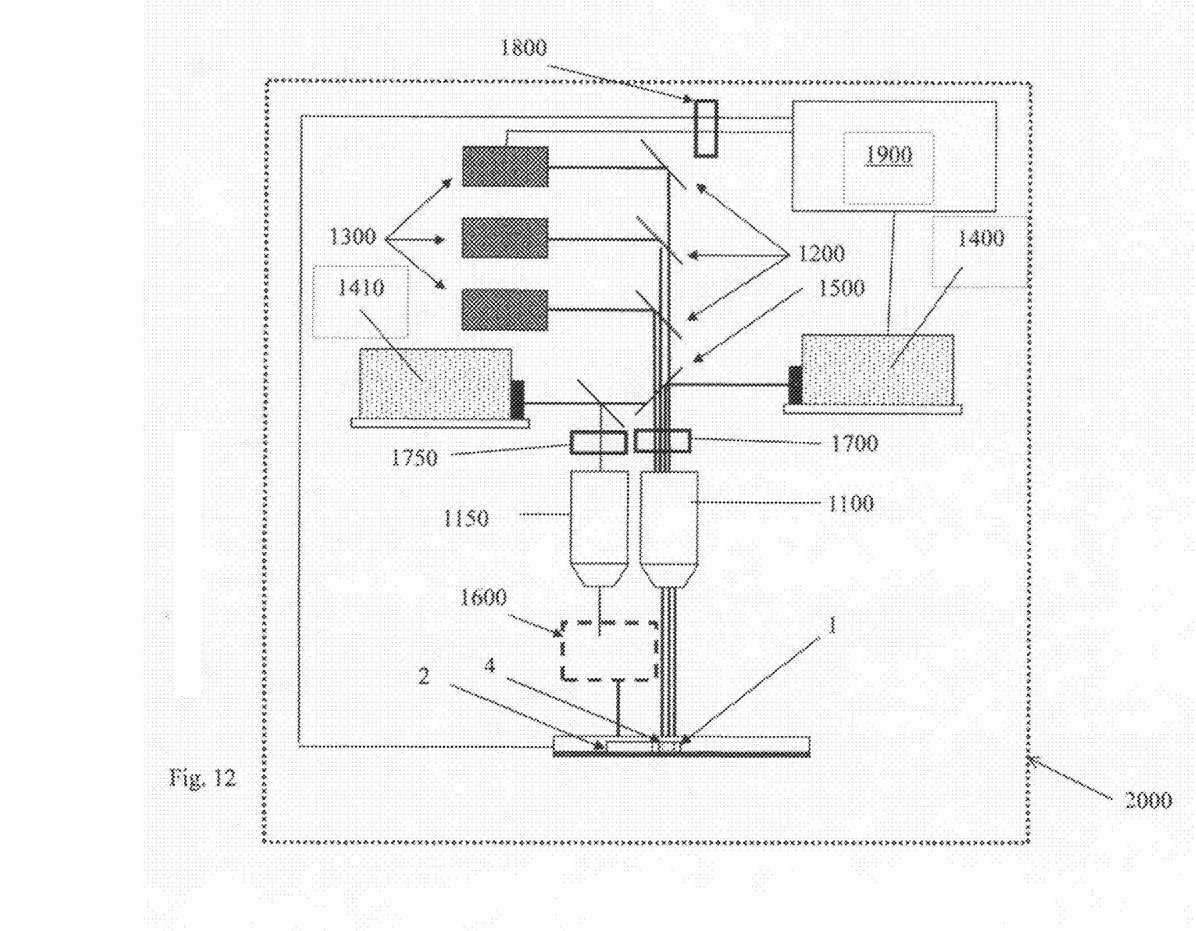
FIG. 12 is a schematic diagram of another embodiment of a particle manipulation system with multiple laser interrogation regions, having multiple laser sources.

FIG. 12 is a schematic diagram of a particle sorting system 2000 which uses a plurality of laser sources 1400 and 1410. One of the laser sources 1410 is used with associated optics 1150 and 1700 to illuminate the at least one additional laser interrogation region 201 and/or 301. This setup may be somewhat more complicated and expensive to arrange than system 1000, but may have advantages in that the optical and detection paths may be separated for the different laser interrogation regions. For this embodiment, it may not be necessary to alter the trajectory, spectral content, timing or duration of the laser 1410 light. Although not shown explicitly in FIG. 12, it should be understood that the detection path for additional laser(s) 1410 may also be separate from the detection path for laser 1400. Accordingly, embodiment 2000 may include a plurality of laser sources and a plurality of lenses which focus the plurality of laser sources into the interrogation regions.

Thus, a MEMS particle manipulation system may be used in conjunction with one or more additional laser interrogation regions, wherein the additional laser interrogation regions are used to confirm the effectiveness or accuracy of a manipulation stage in manipulating a stream of particles. The one or more additional laser interrogation stages may be used to confirm, control or adjust the manipulation stage. The signals from the additional laser interrogation stages may share portions of the detection path and/or optical path with the first laser interrogation stage, and the signals from each may be separated electronically and handled differently by the logic circuits that control the system.

Using the particle manipulation system with cytometric capability may allow the operator to measure one event number (e.g. the captured event rate post-sort) divided by another event number (e.g. the initial event rate pre-sort) for individual particle types, and to feedback to adjust initial interrogation parameters (e.g. such as x, y, z position and also "open window" length in time) based on this ratio. This method may be used to optimize the yield of the system 1000 or 2000. Alternatively, the operator could measure the event rate post-sort of target cells, divided by total event rate post-sort feedback to adjust initial laser interrogation parameters such as x, y, z position and also "open window" length in time, in order to optimize the purity of the sorting system 1000 or 2000.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A particle sorting system, comprising:
   laser light directed into a first laser interrogation region in first portion of a microchannel formed in a substrate;
   at least one particle manipulation stage formed in the substrate, wherein the particle manipulation stage comprises a MEMS movable structure microfabricated on the substrate, and wherein the MEMS microfabricated movable structure has a characteristic dimension smaller than about 500 microns; and
   laser light directed into at least one additional laser interrogation region formed in a second portion of a microchannel formed in the substrate, wherein the first portion of the microchannel is disposed upstream of the particle manipulation stage, and the second portion of the microchannel is disposed downstream of the particle manipulation stage.

2. The particle manipulation system of claim 1, wherein light collected from the at least one additional laser interrogation region is collected by an optical system which also collects light from the first laser interrogation region.

3. A particle sorting system, comprising:
   laser light directed into a first laser interrogation region in first portion of a microchannel formed in a substrate;
   at least one particle manipulation stage formed in the substrate; and
   laser light directed into at least one additional laser interrogation region formed in a second portion of a microchannel formed in the substrate, wherein the first portion of the microchannel is disposed upstream of the particle manipulation stage, and the second portion of the microchannel is disposed downstream of the particle manipulation stage, and the particle manipulation stage comprises a movable structure microfabricated on the substrate which includes the microfluidic channels, wherein the movable structure comprises a flap fluidic valve which separates a target particle from a remainder of the sample stream, based on a signal from the first laser interrogation region.

4. The particle manipulation system of claim 1, further comprising a photoacoustic modulator, which modulates an amplitude of laser light directed into at least one additional laser interrogation region at a frequency of at least about 2 MHz.

5. The particle manipulation system of claim 1, further comprising a high pass filter and a low pass filter which filters the signal from the at least one additional laser interrogation regions.

6. The particle manipulation system of claim 5, further comprising:
   an envelope detector, which outputs a signal proportional to the amplitude envelope of the modulated light.

7. The particle manipulation system of claim 1, further comprising a plurality of laser sources and a plurality of lenses which focus the plurality of laser sources into the interrogation regions.

8. The particle manipulation system of claim 1, further comprising an optical manipulating means that alters at least one of a trajectory, spectral content, timing or duration of the light directed into the at least one additional laser interrogation region.

9. The particle manipulation system of claim 1, wherein the light directed to the first laser interrogation region shares at least a portion of its optical path with light directed to at least one additional laser interrogation region.

10. The particle manipulation system of claim 1, wherein signals from at least one additional laser interrogation region are coupled to logic circuits, and the logic circuits are coupled to the particle manipulation stage to control, monitor or adjust a sorting process.

11. The particle manipulation system of claim 1, wherein the movable structure comprises a permeable material and moves in response to an electromagnetic force.

12. The particle manipulation system of claim 8, wherein the optical manipulation means comprises at least one of the following: a mirror, a beamsplitter, a prism, a harmonic crystal, a photoacoustic modulator, a Q-switch, a saturable absorber and a filter.

13. The particle manipulation system of claim 1, wherein the light collected from the first laser interrogation region shares at least a portion of its optical path with light collected from at least one additional laser interrogation region.

14. The particle manipulation system of claim 1, further comprising an electronic distinguishing means, wherein the electronic distinguishing means comprises at least one of the following: a signal filter, mixer, phase locked loop, multiplexer, trigger, and a device that can separate or distinguish signals.

15. The particle manipulation system of claim 14, wherein the flap fluidic valve is a MEMS hinge mounted movable member.

16. A method for forming a particle manipulation system, comprising:
    forming a first laser interrogation region in first portion of a microchannel formed in a substrate;
    forming at least one particle manipulation stage in the substrate, wherein the particle manipulation stage comprises a MEMS movable structure and microfluidic channels, wherein the MEMS movable structure has a characteristic dimension smaller than about 500 microns; and
    forming at least one additional laser interrogation region in a second portion of a microchannel formed in the substrate, wherein the first portion of the microchannel is upstream of the particle manipulation stage, and the second portion of the microchannel is downstream of the particle manipulation stage.

17. The method of claim 16, further comprising:
    providing light for the first laser interrogation region;
    providing light for the at least one additional laser interrogation region; and
    collecting the first light and the additional light in a common optical detection system.

18. The method of claim 16, wherein forming the particle manipulation stage comprises forming a microfabricated flap-type fluidic valve which separates a target particle from a remainder of the sample stream, based on a signal from the first laser interrogation region.

19. The method of claim 16, further comprising
    providing a photoacoustic modulator to the at least one additional laser interrogation region, which modulates the amplitude of laser light impinging on at least one additional laser interrogation region at a frequency of at least about 2 MHz.

20. The method of claim 16, further comprising:
    providing a plurality of laser sources for the plurality of laser interrogation regions.

* * * * *